United States Patent [19]

Gronostajski

[11] Patent Number: 4,778,458
[45] Date of Patent: Oct. 18, 1988

[54] DISPOSABLE SANITARY ABSORBENT INCONTINENCE PAD

[75] Inventor: David E. Gronostajski, Trenton, N.J.
[73] Assignee: Whitestone Products, Piscataway, N.J.
[21] Appl. No.: 39,139
[22] Filed: Apr. 16, 1987
[51] Int. Cl.[4] ............................................. A61F 13/16
[52] U.S. Cl. ..................................... 604/366; 427/394
[58] Field of Search ............... 604/365, 366, 367, 370, 604/371, 372, 378, 381, 385.1; 427/394

[56] References Cited

U.S. PATENT DOCUMENTS

| | | |
|---|---|---|
| 3,180,335 | 7/1961 | Duncan et al. |
| 3,629,039 | 12/1971 | Frick . |
| 3,758,363 | 9/1973 | Frick . |
| 3,799,167 | 3/1974 | Miller et al. |
| 3,860,003 | 1/1975 | Buell . |
| 4,075,382 | 2/1978 | Chapman et al. |
| 4,112,153 | 9/1978 | Butterworth et al. |
| 4,287,251 | 9/1981 | King et al. |
| 4,392,862 | 7/1983 | Marsan et al. |
| 4,392,908 | 7/1983 | Dehnel . |
| 4,503,098 | 3/1985 | Potts . |
| 4,578,071 | 3/1986 | Buell . |
| 4,627,847 | 12/1986 | Puletti et al. |

FOREIGN PATENT DOCUMENTS 607709  3/1985  Japan .

*Primary Examiner*—John D. Yasko
*Attorney, Agent, or Firm*—Francis J. Bouda

[57] ABSTRACT

A coverstock for disposable sanitary absorbent products is described. It comprises a non-woven web having a body-contacting surface and a material-contacting surface. The web is partially impregnated in selected areas with a fluid-repellent material such as a hot-melt adhesive. The penetration of the repellent material extends from the material-contacting surface, a distance toward the body-contacting surface at least 5% and not more than 95% of the thickness of the web so that the body-contacting surface is free of fluid-repellent material, and so that the material-contacting surface can be secured to the material by application of heat and without any additional adhesive material. A disposable absorbent pad made with the coverstock material, and the process for making the coverstock material and the pad are also disclosed.

6 Claims, 2 Drawing Sheets

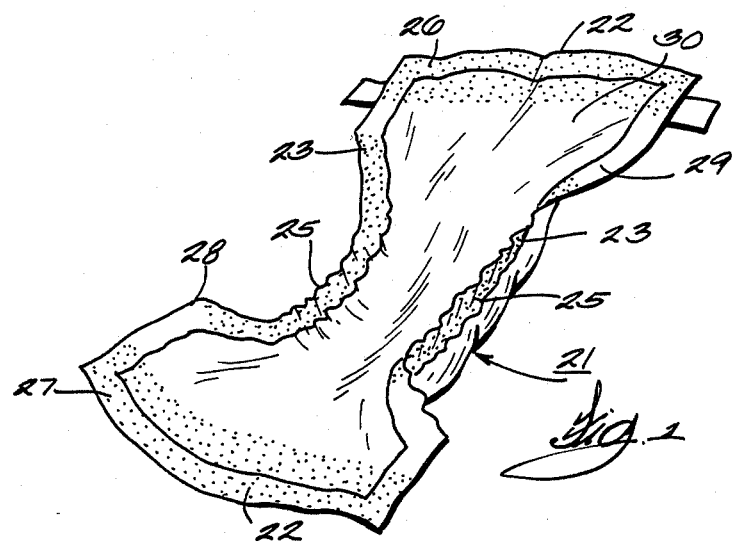
Fig. 1
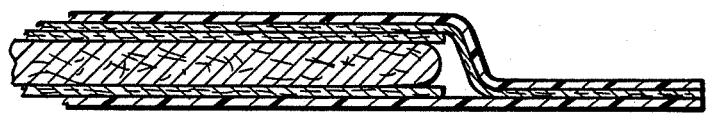
Fig. 11 PRIOR ART
Fig. 8
Fig. 12
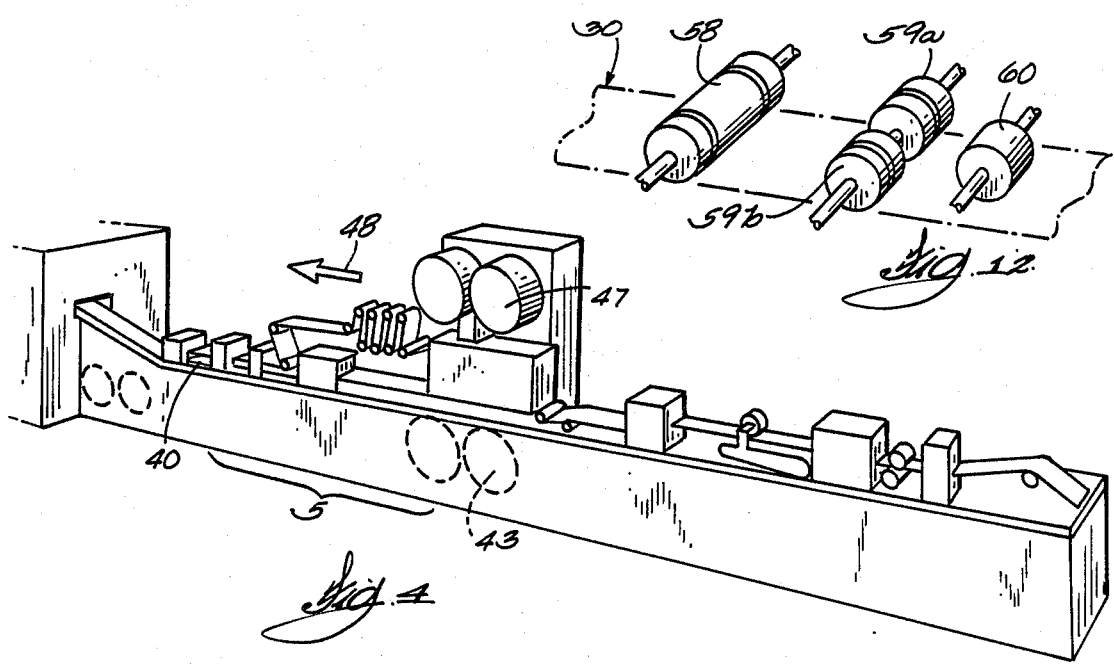
Fig. 4

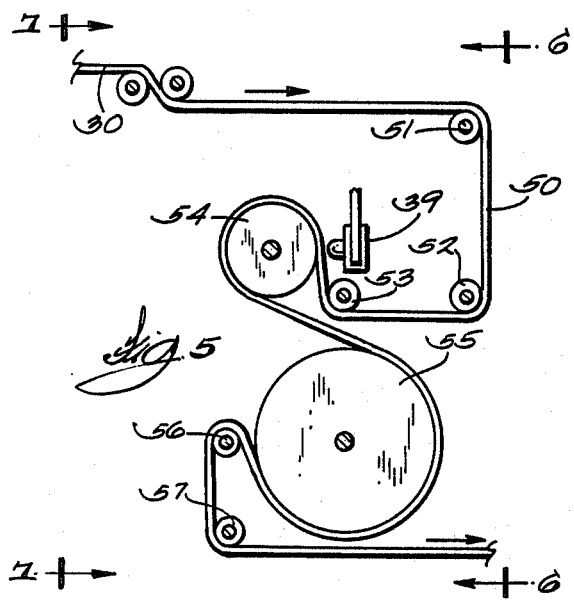
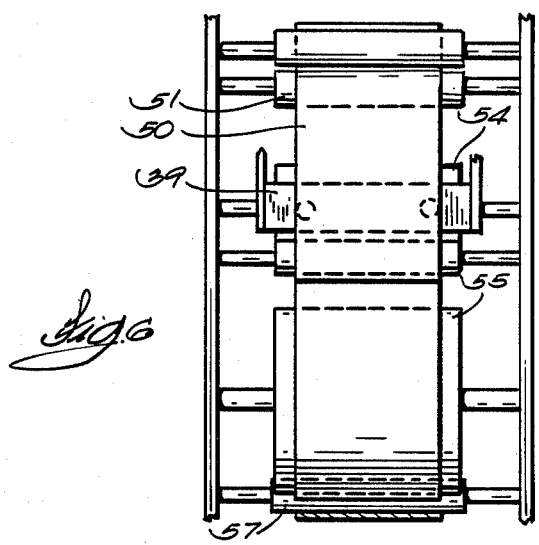
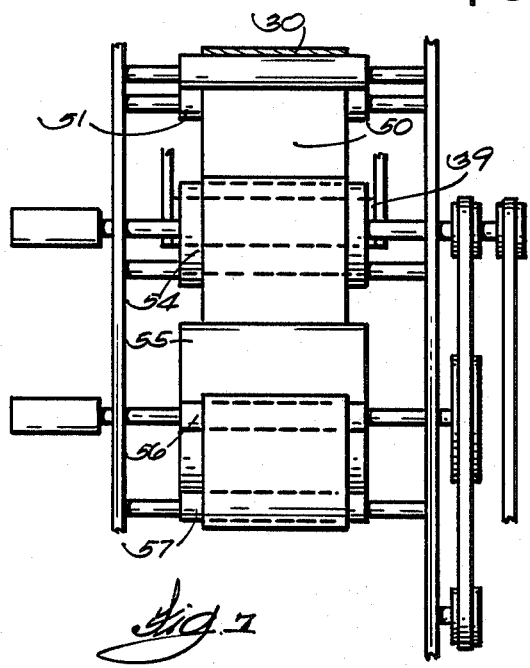
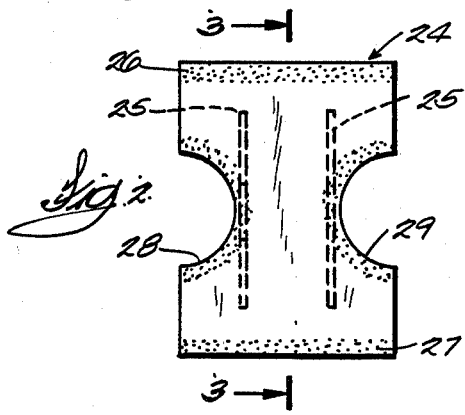
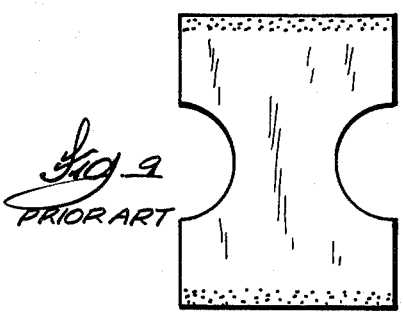
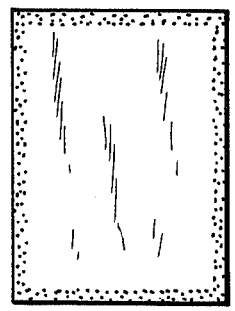
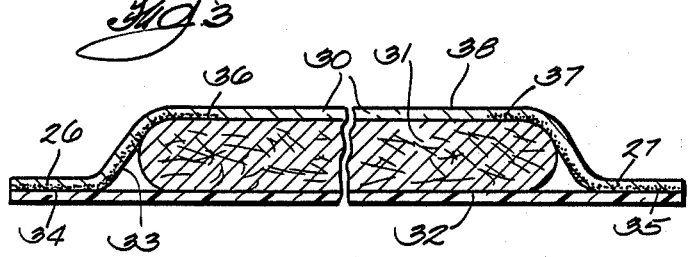

4,778,458

DISPOSABLE SANITARY ABSORBENT INCONTINENCE PAD

BACKGROUND OF THE INVENTION

Disposable sanitary absorbent pads for babies, adults, and hospitalized patients are not new.

The disposable baby diaper business, started by Procter & Gamble 25 years ago, now exceeds sales of 3 billion dollars per year. "LUVS", "PAMPERS", "HUGGIES", and a plethora of private label products are well-known. Literally hundreds of patents have issued on various aspects of the apparatus, process and product.

Within the last five years, the market for disposable sanitary absorbent pads for incontinent adults has grown tremendously and presently exceeds ¼ of a billion dollars per year.

Patents illustrative of the products and the market are the Duncan U.S. Pat. No. 3,180,335 and the Buell U.S. Pat. No. 3,860,003.

The present invention relates particularly to a superior product, and the construction and process for providing a more leak-proof diaper or pad. Jonnson & Johnson's EPA No. 104906, Unicharm's Jap. Pat. No. SH060-7709, Kimberly-Clark's Fricke U.S. Pat. Nos. 3,629,039 and 3,758,363, Miller U.S. Pat. No. 3,799,167, National Starch's Puletti U.S. Pat. No. 4,627,847 and Procter & Gamble's Buell U.S. Pat. No. 4,578,071, are relevant.

The Johnson & Johnson patent is directed particularly to providing a "breathable" backsheet which is water impervious, but also permits a passage of air.

Kimberly-Clark's patents disclose the process and apparatus for applying a thin blue film of polyethylene to an absorbent pad.

The Miller patent shows how a nonwoven web can be totslly impregnated around its entire periphery to provide a fluid-tight border. Puletti is limited to an "end-dam".

The Procter & Gamble patent is directed particularly to a leak-proof perimeter construction which has a series of compacted portions.

SUMMARY OF THE INVENTION

The disposable sanitary absorbent pad of the present invention can be considered either as a baby diaper, an adult incontinence pad, a hospital bed pad, or the like. In all structures there is a similarity because the pad includes a thin, polyethylene backing sheet on one side, and a pervious, hydrophobic cover material on the other side of a central absorbent core. The core can be made of such materials as cellulose fluff, crepe wadding, hydrophylic foam or the like.

It is an object of the present invention to provide a coverstock which is partially impregnated with a water repellent material, and which prevents moisture wicking towards the ends of the product. The water repellent portion penetrates the impervious coverstock material to only a portion of its depth (i.e., thickness) so that while preventing the passage of fluid therethrough, it does not make the material stiff and rough. Furthermore, the construction of a disposable pad made with such a coverstock is arranged so that the impregnant is applied only in the waist and leg portions where needed, and thus afford great economy of production. The process also applies the impregnant in such a manner that the impregnant acts as a mechanism for bonding the coverstock and the impervious plastic backing sheet together, and thus further saves money by not requiring additional glue lines or the like to bond the portions of the pad together and in actuality can allow the elimination of the aforementioned glue lines in the impregnant contact area.

All of the foregoing can be accomplished by slight modifications to the existing equipment and machinery, and, therefore, the capital investment is low.

With the above and other objects in view, more information and a better understanding of the present invention may be achieved by reference to the following detailed description.

DETAILED DESCRIPTION

For the purpose of illustrating the invention, there is shown in the accompanying drawings a form thereof which is at present preferred, although it is to be understood that the several instrumentalities of which the invention consists can be variously arranged and organized and that the invention is not limited to the precise arrangements and organizations of the instrumentalities as herein shown and described.

In the drawings, wherein like reference characters indicate like parts:

FIG. 1 is a perspective view of a disposable baby diaper with the waist-shield/leg-shield construction of the present invention.

FIG. 2 is a schematic top plan view of a baby diaper in its flat (i.e. not contracted) condition, illustrating the waist-shield/leg-shield arrangement.

FIG. 3 is a cross section of a pad taken generally along line 3—3 of FIG. 2 illustrating the construction of a pad made according to the present invention.

FIG. 4 is a stylized perspective view of the type of machine for the production of disposable baby diapers of the type referred to herein.

FIG. 5 is a side elevational view of that portion of the machine in FIG. 4 indicated generally at the area marked "5" therein.

FIG. 6 is a vertical elevational view taken generally along line 6—6 of FIG. 5.

FIG. 7 is a vertical elevational view taken generally along line 7—7 of FIG. 5.

FIG. 8 is a greatly enlarged cross-sectional view of a nonwoven cover material impregnated according to the teachings of the present invention.

FIG. 9 is a schematic view of a baby diaper made according to the prior art with a polyethylene film waist barrier.

FIG. 10 is a schematic view of a prior art bed pad having a full-perimeter waste-barrier.

FIG. 11 is an enlarged cross-sectional view of the waist barrier made according to the prior art referred to in FIG. 9.

FIG. 12 is a schematic perspective view of the compression rolls used to assure the bonding of the diaper coverstock to the diaper backsheet.

In FIG. 1, a disposable baby diaper 21, well known in the art, includes a waist-shield 22 and leg-shields 23 made according to the present invention.

It is to be understood that a diaper of this general nature can be constructed also with elastic waist-bands not shown in FIG. 2 and elastic leg-bands illustrated at 25 in FIG. 2. Such elasticating mechanism, however, is well known in the art and is not more fully described in this specification.

In FIGS. 1 and 2, one can see that the waist areas 26 and 27 and the leg areas 28 and 29 have the coverstock material 30 impregnated according to the present invention.

The purpose of providing this waist-shield/leg-shield construction is to provide a "pocket" or "pouch" for an absorbent pad 31 shown in FIG. 3. This absorbent pad 31 is enclosed within a bottom plastic backing sheet 32 and the top coverstock material 30.

The coverstock material 30 has the portions 26, 27, 28 and 29 partially impregnated, and where these portions extend beyond the absorbent pad 31, as shown in FIG. 3, the coated portion 33 of the portions 26 and 27 contacts the plastic backing sheet 32, sealing those portions together, as at 34 and 35.

The partially impregnated portions of the nonwoven material overlie only a portion of the pad 31, as at 36 and 37 in FIG. 3, leaving the unimpregnated portion 38 free to pass fluid from the patient, baby, or adult, to the pad 31 where it is absorbed.

Generally speaking, the nonwoven material is a type using any of the existing manufacturing techniques applicable to disposable absorbent products and preferably about 17.5 g/yd$^2$, having a thickness of 0.003" to 0.007" of the types supplied by the Scott Paper Company, Kendall Company, James River Co. and others.

The coating is applied to a coverage weight of between 0.010 g/in$^2$ and 0.040 g/in$^2$ or approximately 0.3 mil–0.5 mil thickness (excluding the thickness of the nonwoven substrate).

At this coating weight, the impregnant which is preferably a hot melt utilizing amorphous polypropylene as a base component penetrates the nonwoven to a depth of 0.0010" to 0.0035" or approximately 5% to 95% but less than 100% of the total thickness of the nonwoven.

This provides an integral bond of the hot-melt and the nonwoven, which is extremely supple, but which also permits the sealing or adhesive mechanism between the nonwoven coverstock and the plastic backing to take place.

In the production of a pad according to that above described, the general apparatus may be similar to that shown in the Brody U.S. Pat. No. 4,547,243, the Bouda U.S. Pat. No. 4,353,762, or the Procter & Gamble U.S. Pat. No 4,081,301, and is illustrated in FIG. 4 and includes a carrier mechanism 40 on which a plurality of the absorbent pads 31 are transported.

The polyethylene sheet 32 is brought from an unwind stand 43, and the pads 31 are deposited thereon.

Alternatively, but not preferably, a plurality of thin, glue lines (not shown) can be applied to the top of the plastic sheet 32. These glue lines have, in the past, been used to secure the pads 31 to the plastic sheet, both during the manufacturing process and during later use.

A roll of nonwoven coverstock 30 previously described is shown at 47 where it unwinds in the direction of arrow 48.

A hot-melt applicator 39 is disposed within the loop 50 of the nonwoven web created where the web passes around the turning rolls 51 and 52 and 53 before coming into contact with the application roll 54. The barrier material application at 39 may be of the type manufactured by the Acumeter Labs or the Meltex Company or any other applicator.

The hot melt utilizing amorphous polypropylene may have a melt index of between 160 degrees and 170 degrees Centigrade. As previously mentioned, the hot-melt material is applied in quantities between 0.010 g and 0.040 g. per square inch.

The application roll 54 is constructed as a cooling or metal-jacketed chilling roll with an operating temperature of between 10 degress Fahrenfeit to 40 degrees Fahrenfeit, and the web 30 wraps this roll in a contact arc of between 175 to 350 degrees based on the cooling effect required.

Thereafter, the web passes around another metal jacketed cooling roll 55 which is of larger diameter than the roll 54 and operates at a temperature of between 10 degrees Fahrenfeit and 40 degrees Fahrenfeit in a contact arc of the web of between 170 degrees and 350 degrees, based on the cooling effect required.

Thereafter the web passes around turning rolls 56 and 57 and moves downardly on top of the absorbent pads 31 where it is pressed into close contact with the plastic backing sheet 32 by a series of metal or compressable plastic compression rolls 58, 59-a and 59-b and 60.

During this operation, the linear speed of the web 30 is approximately 200 to 550 feet per minute, and the barrier material application head is applying intermittent portions of hot-melt in cycles of between 100 to 350 per minute.

As can be seen particularly in FIG. 12, the compression rolls 58 and 59 have grooves therein, and these grooves are disposed in such a position that the elastic-leg strands 25 are guided in the grooves and are not compressed by the rolls which press the impregnated nonwoven web into close contact with the polyethylene backing sheet 31.

Roll 60 does not have such a groove because it is disposed generally centrally of the line of movement of the assembled diaper downstream along the machine, and its pressure is applied at the "ends" of the diaper and between the elastic strands.

Appropriate cams or other lifting or guiding mechanism (not shown) are arranged to lift the axis of the rolls 58 and 59 and 60 at appropriate times during the passage of the band of diapers down the machine so that the rolls do not compact the absorbent portion but, where the impregnated nonwoven cover material and polyethylene backing sheet need to be pressed firmly into contact with each other, the rolls are lowered under pressure to apply such compacting forces.

Appropriate timers and control mechanisms, switches, and sensing devices are inter-connected to the drive train, wheels, gears, rolls, applicator head, etc., so that the barrier length and width, thicknesses, quantities and amounts are completely controllable and variable so that the location of the hot-melt on the web, the quantity and pentetration thereof, are carefully controlled.

It is to be understood that the position, location, speed and temperatures of the hot-melt and the cooling rolls 54 and 55 are precisely arranged so that the impregnant does not penetrate less than 5% and not more than 95% of the thickness of the nonwoven, and so that the hot-melt material still remains slightly tacky as the partially-impregnated coverstock material and the plastic backing sheet are brought together between the compression rolls 58, 59 and 60, thus effecting bonding.

The nonwoven cover with its impregnant is laid on top of the pads 31 and the plastic backing sheet 32 with the soft, non-impregnated side of the nonwoven cover uppermost and with the impregnated side facing downwardly so that its comes into contact with the plastic backing sheet 31 and, to a limited portion, in the areas defined and described above, on top of the edges of the absorbent pad 31.

It is of great importance that the nonwoven cover remains supple and soft despite the application of the hot-melt, because the hot-melt is deposited only to a limited depth or a portion of the thickness of the nonwoven, and yet with sufficient amount of the hot-melt render the web impervious in those areas.

It is also important that the application of the hot-melt, its control of depth, and the position and application during the process enable the hot-melt to remain sufficiently tacky and warm so that when it comes in contact with the polyethylene carrying the absorbent batt, and is subjected to the closure of pressures of the rolls 58, 59 and 60, that the material also acts as a total end-seal adhesive for the diaper. This eliminates any need for the hot melt for the multi-bead lines previously referred to.

The acceptability of the product is highly dependent upon the compatibility of the hot-melt, the nonwoven material, the plastic backing, and any other hot-melt adhesive used in the construction.

It should be clear from the foregoing but particularly with reference to FIG. 2 that the method can be used to extrude the same type of coating on the nonwoven longitudinally on the pad during its construction, and with application to provide a leg-shields 28 and 29 in the crotch-portion of the diaper. This provides a heretofore non-available barrier to leakage around the leg-portion of the wearer without wasting any material in those portions of the diapers where a barrier mechanism is not required.

It is to be understood that the present invention may be embodied in other specific forms without departing from the spirit or special attributes hereof, and it is therefore desired that the present embodiments be considered in all respects as illustrative, and therefore not restrictive, reference being made to the appended claims rather than to the foregoing description to indicate the scope of the invention.

Having described my invention, what I claim as new and desire to protect by letters patent are the following:

1. A pervious web cover-material for an absorbent, disposable, sanitary product, said web having a thickness and being impregnated with a fluid barrier material on only one side thereof, and said material penetrating into the interior of said web between about 5% to 95% but less than 100% of the web, said impregnated web being soft to the feel on the uncoated surface.

2. The web of claim 1 wherein the material is a hot melt material of an amorphous polypropylene base or other suitable material.

3. The web of claim 1 wherein the hot melt adhesive not only functions as a liquid impervious barrier, but also as an adhesive seal for the nonwoven to the adjacent substrates.

4. A disposable sanitary absorbent pad having an absorbent core and a pervious cover, said cover being partially impregnated with a fluid barrier, said cover overlying said core with a portion of the barrier in contact with the core wherein the barrier penetrates the cover no more than 95% but less than 100% of the thickness of the cover.

5. The pad of claim 4 wherein the barrier is a hot melt material of an amorphous polypropylene base.

6. The process of creating in a pervious non-woven web a portion thereof which is impervious, said process including the step of
   unwinding a web of non-woven material,
   applying a quantity of barrier material on selected portions of said web,
   controlling the quantity of the barrier material so that it penetrates no more than 95% but less than 100% of the thickness of the said web of non-woven material,
   said controlling including passing the said web over at least one metal jacketed cooling surface so as to cause said barrier material to set before it penetrates fully the thickness of the said web,
   said controlling to include leaving a thin layer of tacky impregnate available for bonding to substrate materials, said controlling including passing the constructed web over a series of relieved metal or compressable plastic compression rolls to effect nonadherence of an elastic thread to the impregnate.

* * * * *